(12) United States Patent
Sawada et al.

(10) Patent No.: US 7,585,674 B2
(45) Date of Patent: Sep. 8, 2009

(54) HOST MICROORGANISMS

(75) Inventors: Kazuhisa Sawada, Haga-gun (JP); Keiji Endo, Haga-gun (JP); Tadahiro Ozawa, Haga-gun (JP); Masatoshi Tohata, Haga-gun (JP); Katsuya Ozaki, Haga-gun (JP)

(73) Assignee: Kao Corporation, Tokyo (JP)

( * ) Notice: Subject to any disclaimer, the term of this patent is extended or adjusted under 35 U.S.C. 154(b) by 40 days.

(21) Appl. No.: 10/479,214

(22) PCT Filed: May 28, 2002

(86) PCT No.: PCT/JP02/05151

§ 371 (c)(1),
(2), (4) Date: Dec. 1, 2003

(87) PCT Pub. No.: WO02/097064

PCT Pub. Date: Dec. 5, 2002

(65) Prior Publication Data

US 2004/0248279 A1 Dec. 9, 2004

(30) Foreign Application Priority Data

May 29, 2001 (JP) .............................. 2001-160520

(51) Int. Cl.
*C12N 5/06* (2006.01)
*G01N 33/53* (2006.01)

(52) U.S. Cl. ........................................ 435/435; 435/7.1

(58) Field of Classification Search ................. 530/350, 530/300; 435/317, 221, 243, 252.1, 252.3, 435/252.31, 69.1, 832–839
See application file for complete search history.

(56) References Cited

U.S. PATENT DOCUMENTS 5,212,083 A * 5/1993 Haldenwang ................ 435/207
5,891,701 A    4/1999 Sloma et al.
6,096,306 A * 8/2000 Bravo et al. ............. 424/93.461

FOREIGN PATENT DOCUMENTS

EP        492274        7/1992

JP    2000-210081 A    8/2000

OTHER PUBLICATIONS

Hakamada et al.( Bioscience Biotechnology Biochemistry vol. 64, No. 11, pp. 2281-2289, 2000).*
Sequence alignment AB018420.*
Attwood, T. K. (Science vol. 290,) Oct. 20, 2000).*
T.J. Kenney et al.: "Organization and regulation of an operon that encodes a sporulation-essential sigma factor in *Bacillus subtilis*" J. Bacteriol., vol. 169, No. 7, pp. 3329-3339, 1987.
K.T. Min et al.: "Activity of mutant sigma F proteins truncated near the C terminus" J. Bacteriol., vol. 174, No. 22, pp. 7144-7148 Nov. 1992.
I. Barak et al.: "SpoIIE mutants of *Bacillus subtilis* comprise two distinct phenotypic classes consistent with a dual functional role for the SpoIIE protein" J. Bacteriol., vol. 178, No. 16, pp. 4984-4989, Aug. 1996.
H. Takamatsu et al.: "The *Bacillus subtilis* yabG gene is transcribed by SigK RNA polymerase during sporulation, and yabG mutant spores have altered coat protein composition" J. Bacteriol., vol. 182, No. 7, pp. 1883-1888, Apr. 2000.
J.H. Kim et al.: "Construction of spore mutants of *Bacillus subtilis* for the development as a host for foreign protein production" Biotechnology Letters, vol. 23, No. 12, pp. 999-1004, Jun. 2001.
M. K. Oh, et al. "Importance of Spore Mutants for Fed-Batch and Continuous Fermentation of *Bacillus subtilis*", Biotechnology and Bioengineering, vol. 47, No. 6, Sep. 20, 1995, pp. 696-702.

* cited by examiner

*Primary Examiner*—Robert Mondesi
*Assistant Examiner*—Khatol Shahnan-Shah
(74) *Attorney, Agent, or Firm*—Oblon, Spivak, McClelland, Maier & Neustadt, P.C.

(57) ABSTRACT

A microorganism wherein one or more genes selected from the group of genes participating in sporulation in the middle to late stages of sporulation have been deleted or inactivated; and a process for producing a target product (a protein) by use the microorganism. No spore is formed when this microorganism is employed, thereby enabling production of a target product (a protein) while decreasing energy loss, production of a by-product and specific production speed to decrease unnecessary consumption of a medium. Moreover, the production period can be prolonged, whereby the target product (the protein) can be produced efficiently.

17 Claims, No Drawings

HOST MICROORGANISMS

This application is a national-stage filing of PCT/JP02/05151, filed May 28, 2002. This application also claims priority to Japan 2001-160520, filed May 29, 2001.

TECHNICAL FIELD

The present invention relates to a host microorganism which is useful for the production of useful proteins or polypeptides, and to a recombinant microorganism.

BACKGROUND ART

Microorganisms have been employed in the industrial production of a broad range of useful substances. For example, microorganisms have been used to produce not only alcoholic beverages and foods such as miso (fermented soy paste) and shoyu (soy sauce), but also amino acids, organic acids, nucleic acid-related substances, antibiotics, sugars, lipids, proteins, and many other types of substances. Use of such substances can be found in a wide range of fields, encompassing foods, pharmaceuticals, daily necessaries such as detergents and cosmetics, and a variety of raw materials for producing items through chemical processes.

One important issue in the industrial production of useful substances through use of microorganisms is improvement in productivity. Thus, as a measure therefor, cultivation of substance-producing microorganisms has been performed through traditional genetic techniques such as mutation. In particular, thanks to progress in microbial genetics and biotechnology, such cultivation of substance-producing microorganisms is now being carried out more efficiently than ever by use of a genetic technologies such as a genetic engineering technology, giving rise to development of host microorganisms useful for genetic recombination. For example, there has been developed a microorganism strain, which resulted from improvement of a microorganism strain *Bacillus subtilis* Marburg No. 168 that had been acknowledged to be safe and excellent.

Microorganisms harbor a diversity of genes, so that they can adapt themselves to environmental changes in the natural kingdom. Therefore, substance productivity of microorganisms cannot necessarily be said to be efficient in terms of industrial production of proteins or similar substances employing limited types of production medium.

Also, concerning certain types of microorganisms, there have been established strains in which genes participating in early stage sporulation are singly deleted or inactivated. However, these strains will not be said to be sufficiently improved in productivity.

Accordingly, an object of the present invention is to provide a host microorganism with which production of proteins or polypeptides can be increased through removal of genes which are useless or harmful in the production of proteins or polypeptides from the genome or inactivation of such genes. Another object of the present invention is to provide a recombinant microorganism produced by incorporating, into the above-mentioned host microorganism, a gene which codes for a protein or polypeptide and which is ligated to a transcription initiation regulation region, translation initiation regulation region, or secretion signal region at the downstream end of the region. Yet another object of the present invention is to provide a method for producing a protein or polypeptide by use of the recombinant microorganism.

DISCLOSURE OF THE INVENTION

The present inventors have extensively searched, among a variety of genes encoded on a microorganism genome, for genes which are useless or function harmfully in the production of useful proteins or polypeptides, and have found that productivity of a protein or polypeptide of interest can be enhanced by deleting from the genome a specific gene participating in sporulation or by inactivating the gene, and then incorporating into the microorganism a gene which encodes a target protein or polypeptide and which has been ligated to a suitable transcriptional initiation region, a translational initiation region, or a secretion signal region, as compared with the productivity attained by the microorganism without such deletion or inactivation.

Accordingly, the present invention provides a microorganism in which one or more genes selected from the genes which participate in sporulation in the middle to late stages of sporulation have been deleted or inactivated; a recombinant microorganism obtained by incorporating, into the gene-deleted or gene-inactivated microorganism, a gene which encodes a protein or polypeptide and which has been ligated to a transcription initiation regulation region, a translation initiation regulation region, or a secretion signal region at the downstream end of the region; and a method for producing a protein or polypeptide through use of the recombinant microorganism.

BEST MODE FOR CARRYING OUT THE INVENTION

No limitations are imposed on the parental microorganism which is used to construct the microorganism of the present invention, so long as it has a gene which participates in sporulation. Preferably, the parental microorganism is a spore-forming microorganism. The parental microorganism may be a wild type or a mutant. Specific examples include bacteria belonging to the genus *Bacillus* such as *Bacillus subtilis*, bacteria belonging to the genus *Clostridium*, and yeasts, with bacteria belonging to the genus *Bacillus* being preferred. Among them, *Bacillus subtilis* is particularly preferred, in view that its complete genome information has already been elucidated, that techniques of genetic engineering and genomic engineering have been established, and that bacteria belonging to the *Bacillus subtilis* have an ability to secrete proteins outside the cells.

Examples of the target protein or polypeptide which is produced by use of the microorganism of the present invention include enzymes which are useful for foodstuffs, drugs, cosmetics, detergents, fiber treatment, drugs for medical tests, etc.; and proteins and polypeptides such as physiological active factors.

Two hundred and fifty or more genes discretely present on the genome have been identified to take part in sporulation. Among them, a target gene to be deleted or inactivated in the present invention is preferably a gene that promotes sporulation, and examples of such a gene include those encoding a sporulation-stage-specific σ-factor, genes participating in expression of any of the σ-factor genes, and genes participating in activation of any of the σ-factors. In addition, genes which are transcribed by any of the σ-factors to thereby participate in promotion of sporulation are also included within the scope of the present invention. In the early stage of sporulation (stages 0-I), extracellular enzymes such as proteases and amylases have been known to be produced in increased amounts as compared with the amounts produced in logarithmic growth phases. Therefore, a target gene to be deleted or inactivated is preferably one or more genes which are expressed specifically in the middle to late stages of sporulation to thereby participate in sporulation. Specifically, a target gene is preferably one or more genes involved in the sporulation stage II, III, IV, or V, more preferably stage II or III, particularly preferably stage II. The present inventors have found that these genes are not directly involved in production of proteins of interest and are also not required for growth of the microorganisms in ordinary medium for industrial production.

Such genes of *Bacillus subtilis* are listed in Tables 1 and 2.

In the present specification, names, sites, base numbers, and functions of the genes are described on the basis of the *Bacillus subtilis* genome database that has been reported in Nature, 390, 249-256 (1997) and also published on-line by JAFAN: Japan Functional Analysis Network for *Bacillus subtilis* (BSORF DB).

TABLE 1

| Gene | Site (kb) | Function |
| --- | --- | --- |
| sigE | 1,604 | Stage II, mother cell-specific σE factor |
| sigF | 2,443 | Stage II, forespore-specific σF factor |
| spoIISB | 1,328 | Stage II and subsequent stages, participating in sporulation |
| spoIIE | 71 | Stage II, activating forespore-specific σF factor |
| sigG | 1,605 | Stages III-V, forespore-specific σG factor |
| spoIVCB-spoIIIC | 2,652-2,701 | Stages IV-V, mother cell-specific σK factor |

TABLE 2

| Gene | Site (kb) | Function |
| --- | --- | --- |
| spoIIGA | 1,604 | Stage II, activating mother cell-specific σE factor |
| spoIIAA | 2,444 | Stage II, participating in activation of forespore-specific σF factor |
| spoIVFB | 2,855 | Stages IV-V, activating mother cell-specific σK factor |
| SpoIIR | 3,794 | Stage II, participating in activation of mother cell-specific σE factor |
| SpoIIIJ | 4,213 | Stages III-V, participating in activation of forespore-specific σG factor |

The following genes are considered to be equivalent to the genes listed in Table 1: Genes having the same functions as those of the *Bacillus subtilis* genes listed in Table 1 or 2, and genes derived from other microorganisms, preferably derived from a bacterium which belongs to the genus *Bacillus*, and exhibiting 70% or more homology, preferably 80% or more, more preferably 90% or more homology, with one of the genes listed in Table 1. These genes are included in the genes which are to be deleted or inactivated according to the present invention. Homology between amino acid sequences is calculated through the Lipman-Pearson method (Science, 227, 1435 (1985)).

When one or more genes selected from among the genes described above are deleted or inactivated, chemical energy consumption required for sporulation of the microorganism is reduced, production period of proteins or polypeptides is prolonged, or other benefits are obtained, resulting in improved productivity of the proteins or polypeptides.

No limitations are imposed on the number of the genes which are deleted or inactivated, so long as at least one gene is deleted or inactivated. The number may be three or more, or five or more. The number is preferably two or three, particularly preferably two.

In order to construct the microorganism of the present invention, one or more genes in addition to the above genes may be deleted or inactivated. Through such a combination, a greater effect in improvement of the productivity could be expected.

Deletion or inactivation of a gene can be performed through known methods. Examples include a method in which target genes are sequentially deleted or inactivated, and a method in which one or more arbitrary DNA fragments are deleted or mutated for inactivation and the resultant gene is analyzed and evaluated in terms of the protein productivity by means of a suitable technique.

A target gene is deleted or inactivated through, for example, a homologous recombination method. Specifically, a DNA fragment containing a target gene is obtained through cloning by use of a suitable plasmid vector. The obtained DNA fragment is mutated by, among other methods, deleting the entire region of the gene or a portion of the target gene region through a routine gene engineering technique while retaining the DNA fragments connected to the respective ends of the target gene; by causing a nonsense mutation in the structural gene through base substitution, frameshift mutation or the like; or by isolating the target gene fragment through cloning or PCR and inserting a DNA fragment into the isolated target gene fragment. Subsequently, the mutated DNA fragment is introduced into a parental microorganism, to thereby cause homologous recombination with the parental microorganism genome at both regions adjacent to the target gene at the respective ends thereof. Thus, the target gene on the genome can be substituted by a DNA fragment in which the target gene has been deleted or inactivated.

Several methods have been reported for deleting or inactivating a target gene through homologous recombination when a bacteria in Bacillus subtilis is employed as a parental microorganism for producing the microorganism of the present invention (e.g., Mol. Gen. Genet., 223, 268 (1990)). The host microorganism of the present invention can be obtained through repetition of such a method.

Deletion or inactivation of one or more arbitrary DNA fragments can also be performed by obtaining one or more arbitrary DNA fragments from a parental microorganism through cloning and performing homologous recombination by use of the fragments in a manner similar to that described above, or alternatively by radiation of a γ-ray to the parental microorganism.

The recombinant microorganism of the present invention can be obtained by incorporating a gene encoding a target protein or polypeptide (hereinafter referred to as "a target protein or polypeptide gene") to the thus-obtained microorganism (host microorganism) in which one or more genes selected from the genes participating in sporulation in the middle to late stages of sporulation have been deleted or inactivated.

No limitations are imposed on the target protein or polypeptide gene. Examples of such genes include industrially usable enzymes such as enzymes for producing detergents, food, fibers, feed, and chemicals, for medical use, and for diagnosis, and physiologically active peptides. The industrially usable enzymes may be classified, on the basis of their functions, into oxidoreductases, transferases, hydrolases, lyases, isomerases, ligases/synthetases, and others. Preferred examples of the target protein or polypeptide gene include genes encoding a hydrolase such as a cellulase, an α-amylase, or a protease. Specific examples include cellulases belonging to the family 5 in Classification of polysaccharide hydrolases (Biochem. J., 280, 309 (1991)). Among them, cellulases derived from a microorganism, particularly cellulases derived from a bacterium belonging to the genus *Bacillus* are illustrated. More specific examples include alkaline cellulases derived from a bacterium belonging to the genus *Bacillus* and having a sequence of SEQ ID NO: 1 or 3, and cellulases having a sequence having 70% or more, preferably 80% or more, more preferably 90% or more homology with the sequence of SEQ ID NO: 1 or 3. The homology between amino acid sequences is determined through the Lipman-Pearson method (Science, 227, 1435 (1985)). Examples of the α-amylases include α-amylases derived from a microorganism, and liquefaction-type amylases derived from a bacterium belonging to the genus *Bacillus* are particularly preferred. Examples of the proteases include serine proteases and metal proteases derived from a microorganism, particularly derived from a bacterium belonging to the genus *Bacillus*.

A target protein or polypeptide gene is desirably ligated, at the upstream end thereof, to a regulation region participating in transcription or translation of the gene or secretion of the gene product, i.e., a transcriptional initiation regulation region containing a promoter and a transcriptional initiation point, a translation initiation region containing a ribosome binding site and an initiation codon, or a secretion signal peptide region in a suitable form. For example, a target protein or polypeptide gene is desirably ligated to the above regulation regions contained in a cellulase gene derived from a bacterium belonging to the genus *Bacillus* which is described in, for example, Japanese Patent Application Laid-Open (kokai) No. 2000-210081 or Hei 4-190793, and the above regulation regions contained in a region adjacent to the cellulase gene at the upstream end of the gene and having a length of 1 kb or less, preferably 0.6 kb or less. Specifically, a target protein or polypeptide gene is desirably ligated to, among others, a sequence of SEQ ID NO: 1 or a 3, or a base sequence having a certain degree of homology with SEQ ID NO: 1 or 3 and having a regulation function similar to that described above.

The recombinant microorganism of the present invention can be obtained by combining a DNA fragment containing a target protein or polypeptide gene with a suitable plasmid vector and incorporating the recombinant plasmid into a host microorganism cell through a routine transformation method. Alternatively, the recombinant microorganism of the present invention can be obtained by using as the DNA fragment a DNA fragment ligated to a suitable homological region of a host microorganism gene and incorporating the resultant DNA fragment directly into the host microorganism gene.

Production of a target protein or polypeptide through use of the recombinant microorganism of the present invention may be performed by inoculating the recombinant microorganism into a medium containing an assimilable source of carbon and nitrogen and the other essential components, culturing the recombinant microorganism through a conventional method, and, after completion of culture, collecting and purifying the target protein or polypeptide.

As described above, a host microorganism of interest in which a sporulation-related gene has been deleted or inactivated can be produced, and a recombinant microorganism of interest can be produced through use of the host microorganism. In addition, by use of the recombinant microorganism, a useful protein or polypeptide can be produced efficiently. An example case in which α-amylase or cellulase is produced through use of *Bacillus subtilis* will next be specifically described.

For example, when the sigf gene of a bacterium *Bacillus subtilis* (768 bp) encoding an RNA polymerase subunit σF-factor which expresses in a forespore in stage II or subsequent stages of sporulation is to be deleted, the following procedure may be employed.

In the first step, a genome gene is extracted from a host microorganism of a *Bacillus subtilis* strain. Using the genome gene as a template, a DNA fragment at the upstream of the initiation codon of the sigF gene and a DNA fragment at the downstream of the termination codon of the sigf gene are joined by a marker gene such as chloramphenicol resistant gene inserted therebetween through SOE (splicing by overlap extention)—PCR (Gene, 77, 61 (1989)) or other methods.

In the next step, the host bacterium *Bacillus subtilis* is transformed by use of the thus-obtained DNA fragment through a competent method, and the transformant is isolated on the basis of chloramphenicol resistance or other characteristics, to thereby cause homologous recombination in the upstream and downstream regions of the sigf gene to give a transformant in which the sigf gene on the genome is substituted by a marker gene such as a chloramphenicol resistant gene or the like.

Thereafter, into the thus-obtained transformant and the original cell line of *Bacillus subtilis* serving as a control, a plasmid containing a gene encoding α-amylase or cellulase is introduced. The thus-obtained recombinant is incubated under suitable conditions, for example, under shaking in a vegetative medium. The supernatant of the culture solution is measured in terms of α-amylase activity or cellulase activity, and it's productivity is compared with that of the original cell line of *Bacillus subtilis*, to thereby confirm that an increased amount of the target product can be obtained by deleting the sigf gene. When the culture solution is subjected to an isolation and purification procedure, α-amylase and cellulase can be obtained.

EXAMPLES

Example 1

A genomic DNA was extracted from *Bacillus subtilis* 168. Using the extracted gene as a template, a 1.5-kb DNA fragment (A), on the genome, adjacent to the sigF gene (Base No. 2442658←2443425) at the upstream end thereof and a 1.5-kb DNA fragment (B) adjacent to the sigF gene at the downstream end thereof were multiplied. Separately, a 0.9-kb DNA fragment (C) containing a chloramphenicol resistant gene was multiplied using plasmid pC194 as a template. The fragments (A), (C), and (B) were serially ligated in this order, through SOE-PCR, to thereby prepare a 3.9-kb DNA fragment. The *Bacillus subtilis* 168 was transformed using the thus-obtained DNA fragment through a competent method. The transformed *Bacillus subtilis* 168 was cultured on an LB agar medium containing chloramphenicol, and the colonies were isolated as a transformat. The resulting transformant was confirmed through PCR and sequencing to have a genome in which the region containing the sigF gene (2442632-2443318) had been deleted and substituted by the chloramphenicol resistant gene. Separately, each of the following regions on the genome was deleted and substituted by the chloramphenicol resistant gene in a manner similar to that described above: a region (1604136-1604976) containing the sigE gene (1604166→1604885), a region (1347781-1348081) containing a substantial part of the spoIISB gene (1347913←1348083), a region (70537→73018) containing a substantial part of the spoIIE gene (70536→73019), a region (1605083-1605877) containing a substantial part of the sigG gene (1605025→1605807), a region (2652156-2652723) containing the spoIVCB gene (2652262→2652732), or a region (2652156-2701031) containing a region from the spoIVCB gene to the spoIIIC gene (2652262→2701023), to thereby prepare a microorganism in which a gene participating in sporulation is deleted.

A DNA fragment (3.1 kb) of the alkaline cellulase gene derived from Bacillus sp. KSM-S237 (Japanese Patent Application Laid-Open (kokai) No. 2000-210081) was introduced into a shuttle vector pHY300PLK at the cleavage point of restriction enzyme BamHI, to thereby prepare a recombinant plasmid pHY-S237. The plasmid was incorporated through the protoplast method into each of the gene-deleted microorganisms prepared in Example 1 and Bacillus subtilis serving as a control. The thus-obtained microorganism was incubated overnight under shaking at 37° C. in an LB medium mL). The resultant culture solution (0.05 mL) was inoculated to 2×L-maltose medium (50 mL; 2% trypton, 1% yeast extraction, 1% NaCl, 7.5% maltose, 7.5-ppm manganese sulfate 4-5 hydrate, 15-ppm tetracyclin), followed by incubation for three days under shaking at 30° C. After completion of incubation, the cells were removed from the culture solution through centrifugation, and the alkaline cellulase activity of the supernatant was measured to determine the amount of alkaline cellulase secreted outside the cells during incubation. As a result, as shown in Table 3, all of the microorganisms in which a gene participating in sporulation had been deleted were found to secrete an increased amount of alkaline cellulase as compared with the control microorganism Bacillus subtilis 168 (wild type).

TABLE 3

| Deleted gene | Site of the gene (kb) | Amount of alkaline cellulase secreted (relative value) |
|---|---|---|
| sigE | 1,604 | 217 |
| sigF | 2,443 | 212 |
| spoIISB | 1,328 | 140 |
| spoIIE | 71 | 216 |
| sigG | 1,605 | 163 |
| spoIVCB-spoIIIC | 2,652-2,701 | 141 |
| spoIVCB | 2,652 | 141 |
| None (wild type) | — | 100 |

INDUSTRIAL APPLICABILITY

When the microorganism of the present invention is employed, no spores are formed. Therefore, the invention enables production of a target protein or target polypeptide while decreasing energy loss, production of by-products and specific production speed to largely decrease unnecessary consumption of a medium. Moreover, the production period of the protein or polypeptide can be prolonged, whereby the target product can be produced efficiently.

```
                             SEQUENCE LISTING

<160> NUMBER OF SEQ ID NOS: 4

<210> SEQ ID NO 1
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 1
gatttgccga tgcaacaggc ttatatttag aggaaatttc ttttaaatt gaatacggaa        60 taaaatcagg taaacaggtc ctgattttat tttttgagt tttagaga actgaagatt        120 gaataaaag tagaagacaa aggacataag aaaattgcat tagttttaat tatagaaaac      180 gccttttat aattatttat acctagaacg aaaatactgt ttcgaaagcg gtttactata     240
aaaccttata ttccggctct tttttaaaac aggggtaaa aattcactct agtattctaa     300
tttcaacatg ctataataaa tttgtaagac gcaatatgca tctctttttt tacgatatat    360
gtaagcggtt aaccttgtgc tatatgccga tttaggaagg ggggtagatt gagtcaagta    420
gtaataatat agataactta taagttgttg agaagcagga gagcatctgg gttactcaca    480
agttttttta aaactttaac gaaagcactt tcggtaatgc ttatgaattt agctatttga    540
ttcaattact ttaaaaatat ttaggaggta at atg atg tta aga aag aaa aca       593
                                  Met Met Leu Arg Lys Lys Thr
                                                          -25 aag cag ttg att tct tcc att ctt att tta gtt tta ctt cta tct tta    641
```

```
Lys Gln Leu Ile Ser Ser Ile Leu Ile Leu Val Leu Leu Ser Leu
        -20              -15             -10 ttt ccg gca gct ctt gca gca gaa gga aac act cgt gaa gac aat ttt    689
Phe Pro Ala Ala Leu Ala Ala Glu Gly Asn Thr Arg Glu Asp Asn Phe
    -5              -1  1               5                      10 aaa cat tta tta ggt aat gac aat gtt aaa cgc cct tct gag gct ggc    737
Lys His Leu Leu Gly Asn Asp Asn Val Lys Arg Pro Ser Glu Ala Gly
                 15              20              25 gca tta caa tta caa gaa gtc gat gga caa atg aca tta gta gat caa    785
Ala Leu Gln Leu Gln Glu Val Asp Gly Gln Met Thr Leu Val Asp Gln
             30              35              40 cat gga gaa aaa att caa tta cgt gga atg agt aca cac gga tta cag    833
His Gly Glu Lys Ile Gln Leu Arg Gly Met Ser Thr His Gly Leu Gln
         45              50              55 tgg ttt cct gag atc ttg aat gat aac gca tac aaa gct ctt tct aac    881
Trp Phe Pro Glu Ile Leu Asn Asp Asn Ala Tyr Lys Ala Leu Ser Asn
     60              65              70 gat tgg gat tcc aat atg att cgt ctt gct atg tat gta ggt gaa aat    929
Asp Trp Asp Ser Asn Met Ile Arg Leu Ala Met Tyr Val Gly Glu Asn
75              80              85                          90 ggg tac gct aca aac cct gag tta atc aaa caa aga gtg att gat gga    977
Gly Tyr Ala Thr Asn Pro Glu Leu Ile Lys Gln Arg Val Ile Asp Gly
                 95              100             105 att gag tta gcg att gaa aat gac atg tat gtt att gtt gac tgg cat   1025
Ile Glu Leu Ala Ile Glu Asn Asp Met Tyr Val Ile Val Asp Trp His
         110             115             120 gtt cat gcg cca ggt gat cct aga gat cct gtt tat gca ggt gct aaa   1073
Val His Ala Pro Gly Asp Pro Arg Asp Pro Val Tyr Ala Gly Ala Lys
             125             130             135 gat ttc ttt aga gaa att gca gct tta tac cct aat aat cca cac att   1121
Asp Phe Phe Arg Glu Ile Ala Ala Leu Tyr Pro Asn Asn Pro His Ile
         140             145             150 att tat gag tta gcg aat gag ccg agt agt aat aat aat ggt gga gca   1169
Ile Tyr Glu Leu Ala Asn Glu Pro Ser Ser Asn Asn Asn Gly Gly Ala
155             160             165             170 ggg att ccg aat aac gaa gaa ggt tgg aaa gcg gta aaa gaa tat gct   1217
Gly Ile Pro Asn Asn Glu Glu Gly Trp Lys Ala Val Lys Glu Tyr Ala
                 175             180             185 gat cca att gta gaa atg tta cgt aaa agc ggt aat gca gat gac aac   1265
Asp Pro Ile Val Glu Met Leu Arg Lys Ser Gly Asn Ala Asp Asp Asn
         190             195             200 att atc att gtt ggt agt cca aac tgg agt cag cgt ccg gac tta gca   1313
Ile Ile Ile Val Gly Ser Pro Asn Trp Ser Gln Arg Pro Asp Leu Ala
         205             210             215 gct gat aat cca att gat gat cac cat aca atg tat act gtt cac ttc   1361
Ala Asp Asn Pro Ile Asp Asp His His Thr Met Tyr Thr Val His Phe
         220             225             230 tac act ggt tca cat gct gct tca act gaa agc tat ccg tct gaa act   1409
Tyr Thr Gly Ser His Ala Ala Ser Thr Glu Ser Tyr Pro Ser Glu Thr
235             240             245             250 cct aac tct gaa aga gga aac gta atg agt aac act cgt tat gcg tta   1457
Pro Asn Ser Glu Arg Gly Asn Val Met Ser Asn Thr Arg Tyr Ala Leu
                 255             260             265 gaa aac gga gta gcg gta ttt gca aca gag tgg gga acg agt caa gct   1505
Glu Asn Gly Val Ala Val Phe Ala Thr Glu Trp Gly Thr Ser Gln Ala
             270             275             280 agt gga gac ggt ggt cct tac ttt gat gaa gca gat gta tgg att gaa   1553
Ser Gly Asp Gly Gly Pro Tyr Phe Asp Glu Ala Asp Val Trp Ile Glu
         285             290             295
```

-continued

| | | |
|---|---|---|
| ttt tta aat gaa aac aac att agc tgg gct aac tgg tct tta acg aat<br>Phe Leu Asn Glu Asn Asn Ile Ser Trp Ala Asn Trp Ser Leu Thr Asn<br>300                               305                            310 | 1601 |

```
ttt tta aat gaa aac aac att agc tgg gct aac tgg tct tta acg aat       1601
Phe Leu Asn Glu Asn Asn Ile Ser Trp Ala Asn Trp Ser Leu Thr Asn
300                 305                 310 aaa aat gaa gta tct ggt gca ttt aca cca ttc gag tta ggt aag tct       1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa       1697
Asn Ala Thr Asn Leu Asp Pro Gly Pro Asp His Val Trp Ala Pro Glu
                335                 340                 345 gaa tta agt ctt tct gga gaa tat gta cgt gct cgt att aaa ggt gtg       1745
Glu Leu Ser Leu Ser Gly Glu Tyr Val Arg Ala Arg Ile Lys Gly Val
        350                 355                 360 aac tat gag cca atc gac cgt aca aaa tac acg aaa gta ctt tgg gac       1793
Asn Tyr Glu Pro Ile Asp Arg Thr Lys Tyr Thr Lys Val Leu Trp Asp
365                 370                 375 ttt aat gat gga acg aag caa gga ttt gga gtg aat tcg gat tct cca       1841
Phe Asn Asp Gly Thr Lys Gln Gly Phe Gly Val Asn Ser Asp Ser Pro
380                 385                 390 aat aaa gaa ctt att gca gtt gat aat gaa aac aac act ttg aaa gtt       1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct       1937
Ser Gly Leu Asp Val Ser Asn Asp Val Ser Asp Gly Asn Phe Trp Ala
                415                 420                 425 aat gct cgt ctt tct gcc aac ggt tgg gga aaa agt gtt gat att tta       1985
Asn Ala Arg Leu Ser Ala Asn Gly Trp Gly Lys Ser Val Asp Ile Leu
        430                 435                 440 ggt gct gag aag ctt aca atg gat gtt att gtt gat gaa cca acg acg       2033
Gly Ala Glu Lys Leu Thr Met Asp Val Ile Val Asp Glu Pro Thr Thr
                445                 450                 455 gta gct att gcg gcg att cca caa agt agt aaa agt gga tgg gca aat       2081
Val Ala Ile Ala Ala Ile Pro Gln Ser Ser Lys Ser Gly Trp Ala Asn
460                 465                 470 cca gag cgt gct gtt cga gtg aac gcg gaa gat ttt gtc cag caa acg       2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct       2177
Asp Gly Lys Tyr Lys Ala Gly Leu Thr Ile Thr Gly Glu Asp Ala Pro
            495                 500                 505 aac cta aaa aat atc gct ttt cat gaa gaa gat aac aat atg aac aac       2225
Asn Leu Lys Asn Ile Ala Phe His Glu Glu Asp Asn Asn Met Asn Asn
        510                 515                 520 atc att ctg ttc gtg gga act gat gca gct gac gtt att tac tta gat       2273
Ile Ile Leu Phe Val Gly Thr Asp Ala Ala Asp Val Ile Tyr Leu Asp
            525                 530                 535 aac att aaa gta att gga aca gaa gtt gaa att cca gtt gtt cat gat       2321
Asn Ile Lys Val Ile Gly Thr Glu Val Glu Ile Pro Val Val His Asp
    540                 545                 550 cca aaa gga gaa gct gtt ctt cct tct gtt ttt gaa gac ggt aca cgt       2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca       2417
Gln Gly Trp Asp Trp Ala Gly Glu Ser Gly Val Lys Thr Ala Leu Thr
            575                 580                 585 att gaa gaa gca aac ggt tct aac gcg tta tca tgg gaa ttt gga tat       2465
Ile Glu Glu Ala Asn Gly Ser Asn Ala Leu Ser Trp Glu Phe Gly Tyr
                590                 595                 600 cca gaa gta aaa cct agt gat aac tgg gca aca gct cca cgt tta gat       2513
Pro Glu Val Lys Pro Ser Asp Asn Trp Ala Thr Ala Pro Arg Leu Asp
            605                 610                 615
```

-continued

| | | |
|---|---|---|
| ttc tgg aaa tct gac ttg gtt cgc ggt gag aat gat tat gta gct ttt<br>Phe Trp Lys Ser Asp Leu Val Arg Gly Glu Asn Asp Tyr Val Ala Phe<br>620                        625                      630 | 2561 |
| gat ttc tat cta gat cca gtt cgt gca aca gaa ggc gca atg aat atc<br>Asp Phe Tyr Leu Asp Pro Val Arg Ala Thr Glu Gly Ala Met Asn Ile<br>635                        640                      645                      650 | 2609 |
| aat tta gta ttc cag cca cct act aac ggg tat tgg gta caa gca cca<br>Asn Leu Val Phe Gln Pro Pro Thr Asn Gly Tyr Trp Val Gln Ala Pro<br>                        655                      660                      665 | 2657 |
| aaa acg tat acg att aac ttt gat gaa tta gag gaa gcg aat caa gta<br>Lys Thr Tyr Thr Ile Asn Phe Asp Glu Leu Glu Glu Ala Asn Gln Val<br>670                        675                      680 | 2705 |
| aat ggt tta tat cac tat gaa gtg aaa att aac gta aga gat att aca<br>Asn Gly Leu Tyr His Tyr Glu Val Lys Ile Asn Val Arg Asp Ile Thr<br>685                        690                      695 | 2753 |
| aac att caa gat gac acg tta cta cgt aac atg atg atc att ttt gca<br>Asn Ile Gln Asp Asp Thr Leu Leu Arg Asn Met Met Ile Ile Phe Ala<br>700                        705                      710 | 2801 |
| gat gta gaa agt gac ttt gca ggg aga gtc ttt gta gat aat gtt cgt<br>Asp Val Glu Ser Asp Phe Ala Gly Arg Val Phe Val Asp Asn Val Arg<br>715                        720                      725                      730 | 2849 |
| ttt gag ggg gct gct act act gag ccg gtt gaa cca gag cca gtt gat<br>Phe Glu Gly Ala Ala Thr Thr Glu Pro Val Glu Pro Glu Pro Val Asp<br>                        735                      740                      745 | 2897 |
| cct ggc gaa gag acg cca cct gtc gat gag aag gaa gcg aaa aaa gaa<br>Pro Gly Glu Glu Thr Pro Pro Val Asp Glu Lys Glu Ala Lys Lys Glu<br>                        750                      755                      760 | 2945 |
| caa aaa gaa gca gag aaa gaa gag aaa gaa gca gta aaa gaa gaa aag<br>Gln Lys Glu Ala Glu Lys Glu Glu Lys Glu Ala Val Lys Glu Glu Lys<br>                        765                      770                      775 | 2993 |
| aaa gaa gct aaa gaa gaa aag aaa gca gtc aaa aat gag gct aag aaa<br>Lys Glu Ala Lys Glu Glu Lys Lys Ala Val Lys Asn Glu Ala Lys Lys<br>780                        785                      790 | 3041 |
| aaa taatctatta aactagttat agggttatct aaaggtctga tgtagatctt<br>Lys<br>795 | 3094 |
| ttagataacc tttttcttgc ataactggac acagagttgt tattaaagaa agtaag | 3150 |

```
<210> SEQ ID NO 2
<211> LENGTH: 824
<212> TYPE: PRT
<213> ORGANISM: Bacillus sp. KSM-S237

<400> SEQUENCE: 2
```

Met Met Leu Arg Lys Lys Thr Lys Gln Leu Ile Ser Ser Ile Leu Ile
                  -25                          -20                          -15

Leu Val Leu Leu Leu Ser Leu Phe Pro Ala Ala Leu Ala Ala Glu Gly
                  -10                          -5                          -1  1

Asn Thr Arg Glu Asp Asn Phe Lys His Leu Leu Gly Asn Asp Asn Val
     5                        10                        15

Lys Arg Pro Ser Glu Ala Gly Ala Leu Gln Leu Gln Glu Val Asp Gly
20                       25                      30                      35

Gln Met Thr Leu Val Asp Gln His Gly Glu Lys Ile Gln Leu Arg Gly
                  40                          45                      50

Met Ser Thr His Gly Leu Gln Trp Phe Pro Glu Ile Leu Asn Asp Asn
          55                        60                        65

Ala Tyr Lys Ala Leu Ser Asn Asp Trp Asp Ser Asn Met Ile Arg Leu
            70                      75                        80

```
Ala Met Tyr Val Gly Glu Asn Gly Tyr Ala Thr Asn Pro Glu Leu Ile
 85                  90                  95

Lys Gln Arg Val Ile Asp Gly Ile Glu Leu Ala Ile Glu Asn Asp Met
100                 105                 110                 115

Tyr Val Ile Val Asp Trp His Val His Ala Pro Gly Asp Pro Arg Asp
                    120                 125                 130

Pro Val Tyr Ala Gly Ala Lys Asp Phe Phe Arg Glu Ile Ala Ala Leu
            135                 140                 145

Tyr Pro Asn Asn Pro His Ile Ile Tyr Glu Leu Ala Asn Glu Pro Ser
                150                 155                 160

Ser Asn Asn Gly Gly Ala Gly Ile Pro Asn Asn Glu Glu Gly Trp
    165                 170                 175

Lys Ala Val Lys Glu Tyr Ala Asp Pro Ile Val Glu Met Leu Arg Lys
180                 185                 190                 195

Ser Gly Asn Ala Asp Asp Asn Ile Ile Ile Val Gly Ser Pro Asn Trp
                200                 205                 210

Ser Gln Arg Pro Asp Leu Ala Ala Asp Asn Pro Ile Asp Asp His His
            215                 220                 225

Thr Met Tyr Thr Val His Phe Tyr Thr Gly Ser His Ala Ala Ser Thr
            230                 235                 240

Glu Ser Tyr Pro Ser Glu Thr Pro Asn Ser Glu Arg Gly Asn Val Met
245                 250                 255

Ser Asn Thr Arg Tyr Ala Leu Glu Asn Gly Val Ala Val Phe Ala Thr
260                 265                 270                 275

Glu Trp Gly Thr Ser Gln Ala Ser Gly Asp Gly Pro Tyr Phe Asp
                280                 285                 290

Glu Ala Asp Val Trp Ile Glu Phe Leu Asn Glu Asn Asn Ile Ser Trp
                295                 300                 305

Ala Asn Trp Ser Leu Thr Asn Lys Asn Glu Val Ser Gly Ala Phe Thr
            310                 315                 320

Pro Phe Glu Leu Gly Lys Ser Asn Ala Thr Asn Leu Asp Pro Gly Pro
325                 330                 335

Asp His Val Trp Ala Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                360                 365                 370

Tyr Thr Lys Val Leu Trp Asp Phe Asn Asp Gly Thr Lys Gln Gly Phe
            375                 380                 385

Gly Val Asn Ser Asp Ser Pro Asn Lys Glu Leu Ile Ala Val Asp Asn
            390                 395                 400

Glu Asn Asn Thr Leu Lys Val Ser Gly Leu Asp Val Ser Asn Asp Val
            405                 410                 415

Ser Asp Gly Asn Phe Trp Ala Asn Ala Arg Leu Ser Ala Asn Gly Trp
420                 425                 430                 435

Gly Lys Ser Val Asp Ile Leu Gly Ala Glu Lys Leu Thr Met Asp Val
                440                 445                 450

Ile Val Asp Glu Pro Thr Thr Val Ala Ile Ala Ile Pro Gln Ser
            455                 460                 465

Ser Lys Ser Gly Trp Ala Asn Pro Glu Arg Ala Val Arg Val Asn Ala
            470                 475                 480

Glu Asp Phe Val Gln Gln Thr Asp Gly Lys Tyr Lys Ala Gly Leu Thr
485                 490                 495
```

| | | | | | | | | | | | | |
|---|---|---|---|---|---|---|---|---|---|---|---|---|
| Ile | Thr | Gly | Glu | Asp | Ala | Pro | Asn | Leu | Lys | Asn | Ile | Ala | Phe | His | Glu |
| 500 | | | | | 505 | | | | | 510 | | | | | 515 |

| Glu | Asp | Asn | Asn | Met | Asn | Asn | Ile | Ile | Leu | Phe | Val | Gly | Thr | Asp | Ala |
| | | | | 520 | | | | | 525 | | | | | 530 | |

| Ala | Asp | Val | Ile | Tyr | Leu | Asp | Asn | Ile | Lys | Val | Ile | Gly | Thr | Glu | Val |
| | | | | 535 | | | | | 540 | | | | | 545 | |

| Glu | Ile | Pro | Val | Val | His | Asp | Pro | Lys | Gly | Glu | Ala | Val | Leu | Pro | Ser |
| | | | | 550 | | | | | 555 | | | | | 560 | |

| Val | Phe | Glu | Asp | Gly | Thr | Arg | Gln | Gly | Trp | Asp | Trp | Ala | Gly | Glu | Ser |
| | | | | 565 | | | | | 570 | | | | | 575 | |

| Gly | Val | Lys | Thr | Ala | Leu | Thr | Ile | Glu | Glu | Ala | Asn | Gly | Ser | Asn | Ala |
| 580 | | | | | 585 | | | | | 590 | | | | | 595 |

| Leu | Ser | Trp | Glu | Phe | Gly | Tyr | Pro | Glu | Val | Lys | Pro | Ser | Asp | Asn | Trp |
| | | | | 600 | | | | | 605 | | | | | 610 | |

| Ala | Thr | Ala | Pro | Arg | Leu | Asp | Phe | Trp | Lys | Ser | Asp | Leu | Val | Arg | Gly |
| | | | | 615 | | | | | 620 | | | | | 625 | |

| Glu | Asn | Asp | Tyr | Val | Ala | Phe | Asp | Phe | Tyr | Leu | Asp | Pro | Val | Arg | Ala |
| | | | | 630 | | | | | 635 | | | | | 640 | |

| Thr | Glu | Gly | Ala | Met | Asn | Ile | Asn | Leu | Val | Phe | Gln | Pro | Pro | Thr | Asn |
| | | | | 645 | | | | | 650 | | | | | 655 | |

| Gly | Tyr | Trp | Val | Gln | Ala | Pro | Lys | Thr | Tyr | Thr | Ile | Asn | Phe | Asp | Glu |
| 660 | | | | | 665 | | | | | 670 | | | | | 675 |

| Leu | Glu | Glu | Ala | Asn | Gln | Val | Asn | Gly | Leu | Tyr | His | Tyr | Glu | Val | Lys |
| | | | | 680 | | | | | 685 | | | | | 690 | |

| Ile | Asn | Val | Arg | Asp | Ile | Thr | Asn | Ile | Gln | Asp | Asp | Thr | Leu | Leu | Arg |
| | | | | 695 | | | | | 700 | | | | | 705 | |

| Asn | Met | Met | Ile | Ile | Phe | Ala | Asp | Val | Glu | Ser | Asp | Phe | Ala | Gly | Arg |
| | | | | 710 | | | | | 715 | | | | | 720 | |

| Val | Phe | Val | Asp | Asn | Val | Arg | Phe | Glu | Gly | Ala | Ala | Thr | Thr | Glu | Pro |
| | | | | 725 | | | | | 730 | | | | | 735 | |

| Val | Glu | Pro | Glu | Pro | Val | Asp | Pro | Gly | Glu | Glu | Thr | Pro | Pro | Val | Asp |
| 740 | | | | | 745 | | | | | 750 | | | | | 755 |

| Glu | Lys | Glu | Ala | Lys | Lys | Glu | Gln | Lys | Glu | Ala | Glu | Lys | Glu | Glu | Lys |
| | | | | 760 | | | | | 765 | | | | | 770 | |

| Glu | Ala | Val | Lys | Glu | Glu | Lys | Lys | Glu | Ala | Lys | Glu | Glu | Lys | Lys | Ala |
| | | | | 775 | | | | | 780 | | | | | 785 | |

| Val | Lys | Asn | Glu | Ala | Lys | Lys | Lys |
| | | | | 790 | | | | | 795 |

```
<210> SEQ ID NO 3
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)

<400> SEQUENCE: 3
agtacttacc attttagagt caaaagatag aagccaagca ggatttgccg atgcaaccgg     60
cttatattta gagggaattt ctttttaaat tgaatacgga ataaaatcag gtaaacaggt    120 cctgattta ttttttgaa ttttttgag aactaaagat tgaaatagaa gtagaagaca       180
```

-continued

```
acggacataa gaaaattgta ttagttttaa ttatagaaaa cgcttttcta taattattta    240
tacctagaac gaaaatactg tttcgaaagc ggtttactat aaaaccttat attccggctc    300
tttttttaaa caggggtga aaattcactc tagtattcta atttcaacat gctataataa     360
atttgtaaga cgcaatatac atcttttttt tatgatattt gtaagcggtt aaccttgtgc    420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt aataatttta    600
```

```
ggaggtaat atg atg tta aga aag aaa aca aag cag ttg att tct tcc att    651
          Met Met Leu Arg Lys Lys Thr Lys Gln Leu Ile Ser Ser Ile
              -25                  -20 ctt att tta gtt tta ctt cta tct tta ttt ccg aca gct ctt gca gca      699
Leu Ile Leu Val Leu Leu Leu Ser Leu Phe Pro Thr Ala Leu Ala Ala
-15              -10                   -5                -1   1 gaa gga aac act cgt gaa gac aat ttt aaa cat tta tta ggt aat gac      747
Glu Gly Asn Thr Arg Glu Asp Asn Phe Lys His Leu Leu Gly Asn Asp
                5                  10                  15 aat gtt aaa cgc cct tct gag gct ggc gca tta caa tta caa gaa gtc      795
Asn Val Lys Arg Pro Ser Glu Ala Gly Ala Leu Gln Leu Gln Glu Val
        20                  25                  30 gat gga caa atg aca tta gta gat caa cat gga gaa aaa att caa tta      843
Asp Gly Gln Met Thr Leu Val Asp Gln His Gly Glu Lys Ile Gln Leu
    35                  40                  45 cgt gga atg agt aca cac gga tta caa tgg ttt cct gag atc ttg aat      891
Arg Gly Met Ser Thr His Gly Leu Gln Trp Phe Pro Glu Ile Leu Asn
50                  55                  60                  65 gat aac gca tac aaa gct ctt gct aac gat tgg gaa tca aat atg att      939
Asp Asn Ala Tyr Lys Ala Leu Ala Asn Asp Trp Glu Ser Asn Met Ile
                70                  75                  80 cgt cta gct atg tat gtc ggt gaa aat ggc tat gct tca aat cca gag      987
Arg Leu Ala Met Tyr Val Gly Glu Asn Gly Tyr Ala Ser Asn Pro Glu
        85                  90                  95 tta att aaa agc aga gtc att aaa gga ata gat ctt gct att gaa aat      1035
Leu Ile Lys Ser Arg Val Ile Lys Gly Ile Asp Leu Ala Ile Glu Asn
    100                 105                 110 gac atg tat gtc atc gtt gat tgg cat gta cat gca cct ggt gat cct      1083
Asp Met Tyr Val Ile Val Asp Trp His Val His Ala Pro Gly Asp Pro
115                 120                 125 aga gat ccc gtt tac gct gga gca gaa gat ttc ttt aga gat att gca      1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag      1179
Ala Leu Tyr Pro Asn Asn Pro His Ile Ile Tyr Glu Leu Ala Asn Glu
                150                 155                 160 cca agt agt aac aat aat ggt gga gct ggg att cca aat aat gaa gaa      1227
Pro Ser Ser Asn Asn Asn Gly Gly Ala Gly Ile Pro Asn Asn Glu Glu
        165                 170                 175 ggt tgg aat gcg gta aaa gaa tac gct gat cca att gta gaa atg tta      1275
Gly Trp Asn Ala Val Lys Glu Tyr Ala Asp Pro Ile Val Glu Met Leu
    180                 185                 190 cgt gat agc ggg aac gca gat gac aat att atc att gtg ggt agt cca      1323
Arg Asp Ser Gly Asn Ala Asp Asp Asn Ile Ile Ile Val Gly Ser Pro
195                 200                 205 aac tgg agt cag cgt cct gac tta gca gct gat aat cca att gat gat      1371
Asn Trp Ser Gln Arg Pro Asp Leu Ala Ala Asp Asn Pro Ile Asp Asp
210                 215                 220                 225
```

-continued

| | |
|---|---|
| cac cat aca atg tat act gtt cac ttc tac act ggt tca cat gct gct<br>His His Thr Met Tyr Thr Val His Phe Tyr Thr Gly Ser His Ala Ala<br>　　　　230　　　　　　　235　　　　　　　240 | 1419 |
| tca act gaa agc tat ccg cct gaa act cct aac tct gaa aga gga aac<br>Ser Thr Glu Ser Tyr Pro Pro Glu Thr Pro Asn Ser Glu Arg Gly Asn<br>　　　245　　　　　　　250　　　　　　　255 | 1467 |
| gta atg agt aac act cgt tat gcg tta gaa aac gga gta gca gta ttt<br>Val Met Ser Asn Thr Arg Tyr Ala Leu Glu Asn Gly Val Ala Val Phe<br>　260　　　　　　　265　　　　　　　270 | 1515 |
| gca aca gag tgg gga act agc caa gca aat gga gat ggt ggt cct tac<br>Ala Thr Glu Trp Gly Thr Ser Gln Ala Asn Gly Asp Gly Gly Pro Tyr<br>275　　　　　　　280　　　　　　　285 | 1563 |
| ttt gat gaa gca gat gta tgg att gag ttt tta aat gaa aac aac att<br>Phe Asp Glu Ala Asp Val Trp Ile Glu Phe Leu Asn Glu Asn Asn Ile<br>290　　　　　　　295　　　　　　　300　　　　　　　305 | 1611 |
| agc tgg gct aac tgg tct tta acg aat aaa aat gaa gta tct ggt gca<br>Ser Trp Ala Asn Trp Ser Leu Thr Asn Lys Asn Glu Val Ser Gly Ala<br>　　　　310　　　　　　　315　　　　　　　320 | 1659 |
| ttt aca cca ttc gag tta ggt aag tct aac gca aca agt ctt gac cca<br>Phe Thr Pro Phe Glu Leu Gly Lys Ser Asn Ala Thr Ser Leu Asp Pro<br>　　　325　　　　　　　330　　　　　　　335 | 1707 |
| ggg cca gac caa gta tgg gta cca gaa gag tta agt ctt tct gga gaa<br>Gly Pro Asp Gln Val Trp Val Pro Glu Glu Leu Ser Leu Ser Gly Glu<br>　340　　　　　　　345　　　　　　　350 | 1755 |
| tat gta cgt gct cgt att aaa ggt gtg aac tat gag cca atc gac cgt<br>Tyr Val Arg Ala Arg Ile Lys Gly Val Asn Tyr Glu Pro Ile Asp Arg<br>355　　　　　　　360　　　　　　　365 | 1803 |
| aca aaa tac acg aaa gta ctt tgg gac ttt aat gat gga acg aag caa<br>Thr Lys Tyr Thr Lys Val Leu Trp Asp Phe Asn Asp Gly Thr Lys Gln<br>370　　　　　　　375　　　　　　　380　　　　　　　385 | 1851 |
| gga ttt gga gtg aat gga gat tct cca gtt gaa gat gta gtt att gag<br>Gly Phe Gly Val Asn Gly Asp Ser Pro Val Glu Asp Val Val Ile Glu<br>　　　　390　　　　　　　395　　　　　　　400 | 1899 |
| aat gaa gcg ggc gct tta aaa ctt tca gga tta gat gca agt aat gat<br>Asn Glu Ala Gly Ala Leu Lys Leu Ser Gly Leu Asp Ala Ser Asn Asp<br>　　　405　　　　　　　410　　　　　　　415 | 1947 |
| gtt tct gaa ggt aat tac tgg gct aat gct cgt ctt tct gcc gac ggt<br>Val Ser Glu Gly Asn Tyr Trp Ala Asn Ala Arg Leu Ser Ala Asp Gly<br>　420　　　　　　　425　　　　　　　430 | 1995 |
| tgg gga aaa agt gtt gat att tta ggt gct gaa aaa ctt act atg gat<br>Trp Gly Lys Ser Val Asp Ile Leu Gly Ala Glu Lys Leu Thr Met Asp<br>435　　　　　　　440　　　　　　　445 | 2043 |
| gtg att gtt gat gag ccg acc acg gta tca att gct gca att cca caa<br>Val Ile Val Asp Glu Pro Thr Thr Val Ser Ile Ala Ala Ile Pro Gln<br>450　　　　　　　455　　　　　　　460　　　　　　　465 | 2091 |
| ggg cca tca gcc aat tgg gtt aat cca aat cgt gca att aag gtt gag<br>Gly Pro Ser Ala Asn Trp Val Asn Pro Asn Arg Ala Ile Lys Val Glu<br>　　　　470　　　　　　　475　　　　　　　480 | 2139 |
| cca act aat ttc gta ccg tta gga gat aag ttt aaa gcg gaa tta act<br>Pro Thr Asn Phe Val Pro Leu Gly Asp Lys Phe Lys Ala Glu Leu Thr<br>　　　485　　　　　　　490　　　　　　　495 | 2187 |
| ata act tca gct gac tct cca tcg tta gaa gct att gcg atg cat gct<br>Ile Thr Ser Ala Asp Ser Pro Ser Leu Glu Ala Ile Ala Met His Ala<br>　500　　　　　　　505　　　　　　　510 | 2235 |
| gaa aat aac aac atc aac aac atc att ctt ttt gta gga act gaa ggt<br>Glu Asn Asn Asn Ile Asn Asn Ile Ile Leu Phe Val Gly Thr Glu Gly<br>515　　　　　　　520　　　　　　　525 | 2283 |
| gct gat gtt atc tat tta gat aac att aaa gta att gga aca gaa gtt<br>Ala Asp Val Ile Tyr Leu Asp Asn Ile Lys Val Ile Gly Thr Glu Val<br>530　　　　　　　535　　　　　　　540　　　　　　　545 | 2331 |

```
gaa att cca gtt gtt cat gat cca aaa gga gaa gct gtt ctt cct tct          2379
Glu Ile Pro Val Val His Asp Pro Lys Gly Glu Ala Val Leu Pro Ser
            550                 555                 560 gtt ttt gaa gac ggt aca cgt caa ggt tgg gac tgg gct gga gag tct          2427
Val Phe Glu Asp Gly Thr Arg Gln Gly Trp Asp Trp Ala Gly Glu Ser
565                 570                 575 ggt gtg aaa aca gct tta aca att gaa gaa gca aac ggt tct aac gcg          2475
Gly Val Lys Thr Ala Leu Thr Ile Glu Glu Ala Asn Gly Ser Asn Ala
            580                 585                 590 tta tca tgg gaa ttt gga tac cca gaa gta aaa cct agt gat aac tgg          2523
Leu Ser Trp Glu Phe Gly Tyr Pro Glu Val Lys Pro Ser Asp Asn Trp
595                 600                 605 gca aca gct cca cgt tta gat ttc tgg aaa tct gac ttg gtt cgc ggt          2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca          2619
Glu Asn Asp Tyr Val Thr Phe Asp Phe Tyr Leu Asp Pro Val Arg Ala
            630                 635                 640 aca gaa ggc gca atg aat atc aat tta gta ttc cag cca cct act aac          2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa          2715
Gly Tyr Trp Val Gln Ala Pro Lys Thr Tyr Thr Ile Asn Phe Asp Glu
            660                 665                 670 tta gag gaa gcg aat caa gta aat ggt tta tat cac tat gaa gtg aaa          2763
Leu Glu Glu Ala Asn Gln Val Asn Gly Leu Tyr His Tyr Glu Val Lys
675                 680                 685 att aac gta aga gat att aca aac att caa gat gac acg tta cta cgt          2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga          2859
Asn Met Met Ile Ile Phe Ala Asp Val Glu Ser Asp Phe Ala Gly Arg
            710                 715                 720 gtc ttt gta gat aat gtt cgt ttt gag ggg gct gct act act gag ccg          2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat          2955
Val Glu Pro Glu Pro Val Asp Pro Gly Glu Glu Thr Pro Pro Val Asp
740                 745                 750 gag aag gaa gcg aaa aaa gaa caa aaa gaa gca gag aaa gaa gag aaa          3003
Glu Lys Glu Ala Lys Lys Glu Gln Lys Glu Ala Glu Lys Glu Glu Lys
755                 760                 765 gaa gca gta aaa gaa gaa aag aaa gaa gct aaa gaa gaa aag aaa gca          3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct        3105
Ile Lys Asn Glu Ala Thr Lys Lys
            790 aaaggtctga tgcagatctt ttagataacc tttttttgca taactggaca tagaatggtt       3165 attaaagaaa gcaaggtgtt tatacgatat taaaaaggta gcgattttaa attgaaacct       3225 ttaataatgt cttgtgatag aatgatgaag taatttaaga gggggaaacg aagtgaaaac       3285 ggaaatttct agtagaagaa aaacagacca agaaatactg caagctt                    3332

<210> SEQ ID NO 4
<211> LENGTH: 822
<212> TYPE: PRT
<213> ORGANISM: Bacillus sp. KSM-64
```

<400> SEQUENCE: 4

```
Met Met Leu Arg Lys Lys Thr Lys Gln Leu Ile Ser Ser Ile Leu Ile
            -25                 -20                 -15
Leu Val Leu Leu Leu Ser Leu Phe Pro Thr Ala Leu Ala Ala Glu Gly
            -10                  -5                  -1   1
Asn Thr Arg Glu Asp Asn Phe Lys His Leu Leu Gly Asn Asp Asn Val
         5                  10                  15
Lys Arg Pro Ser Glu Ala Gly Ala Leu Gln Leu Gln Glu Val Asp Gly
 20                  25                  30                  35
Gln Met Thr Leu Val Asp Gln His Gly Glu Lys Ile Gln Leu Arg Gly
             40                  45                  50
Met Ser Thr His Gly Leu Gln Trp Phe Pro Glu Ile Leu Asn Asp Asn
             55                  60                  65
Ala Tyr Lys Ala Leu Ala Asn Asp Trp Glu Ser Asn Met Ile Arg Leu
             70                  75                  80
Ala Met Tyr Val Gly Glu Asn Gly Tyr Ala Ser Asn Pro Glu Leu Ile
             85                  90                  95
Lys Ser Arg Val Ile Lys Gly Ile Asp Leu Ala Ile Glu Asn Asp Met
100                 105                 110                 115
Tyr Val Ile Val Asp Trp His Val His Ala Pro Gly Asp Pro Arg Asp
                120                 125                 130
Pro Val Tyr Ala Gly Ala Glu Asp Phe Phe Arg Asp Ile Ala Ala Leu
                135                 140                 145
Tyr Pro Asn Asn Pro His Ile Ile Tyr Glu Leu Ala Asn Glu Pro Ser
                150                 155                 160
Ser Asn Asn Asn Gly Gly Ala Gly Ile Pro Asn Asn Glu Glu Gly Trp
                165                 170                 175
Asn Ala Val Lys Glu Tyr Ala Asp Pro Ile Val Glu Met Leu Arg Asp
180                 185                 190                 195
Ser Gly Asn Ala Asp Asp Asn Ile Ile Ile Val Gly Ser Pro Asn Trp
                200                 205                 210
Ser Gln Arg Pro Asp Leu Ala Ala Asp Asn Pro Ile Asp Asp His His
                215                 220                 225
Thr Met Tyr Thr Val His Phe Tyr Thr Gly Ser His Ala Ala Ser Thr
                230                 235                 240
Glu Ser Tyr Pro Pro Glu Thr Pro Asn Ser Glu Arg Gly Asn Val Met
                245                 250                 255
Ser Asn Thr Arg Tyr Ala Leu Glu Asn Gly Val Ala Val Phe Ala Thr
260                 265                 270                 275
Glu Trp Gly Thr Ser Gln Ala Asn Gly Asp Gly Gly Pro Tyr Phe Asp
                280                 285                 290
Glu Ala Asp Val Trp Ile Glu Phe Leu Asn Glu Asn Asn Ile Ser Trp
                295                 300                 305
Ala Asn Trp Ser Leu Thr Asn Lys Asn Glu Val Ser Gly Ala Phe Thr
                310                 315                 320
Pro Phe Glu Leu Gly Lys Ser Asn Ala Thr Ser Leu Asp Pro Gly Pro
                325                 330                 335
Asp Gln Val Trp Val Pro Glu Glu Leu Ser Leu Ser Gly Glu Tyr Val
340                 345                 350                 355
Arg Ala Arg Ile Lys Gly Val Asn Tyr Glu Pro Ile Asp Arg Thr Lys
                360                 365                 370
Tyr Thr Lys Val Leu Trp Asp Phe Asn Asp Gly Thr Lys Gln Gly Phe
                375                 380                 385
```

```
Gly Val Asn Gly Asp Ser Pro Val Glu Asp Val Ile Glu Asn Glu
            390                 395                 400

Ala Gly Ala Leu Lys Leu Ser Gly Leu Asp Ala Ser Asn Asp Val Ser
405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
                440                 445                 450

Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
        470                 475                 480

Asn Phe Val Pro Leu Gly Asp Lys Phe Lys Ala Glu Leu Thr Ile Thr
    485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
                520                 525                 530

Val Ile Tyr Leu Asp Asn Ile Lys Val Ile Gly Thr Glu Val Glu Ile
            535                 540                 545

Pro Val Val His Asp Pro Lys Gly Glu Ala Val Leu Pro Ser Val Phe
        550                 555                 560

Glu Asp Gly Thr Arg Gln Gly Trp Asp Trp Ala Gly Glu Ser Gly Val
    565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
                600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
        630                 635                 640

Gly Ala Met Asn Ile Asn Leu Val Phe Gln Pro Pro Thr Asn Gly Tyr
    645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
                680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
        710                 715                 720

Val Asp Asn Val Arg Phe Glu Gly Ala Ala Thr Thr Glu Pro Val Glu
    725                 730                 735

Pro Glu Pro Val Asp Pro Gly Glu Glu Thr Pro Val Asp Glu Lys
740                 745                 750                 755

Glu Ala Lys Lys Glu Gln Lys Glu Ala Glu Lys Glu Lys Glu Ala
                760                 765                 770

Val Lys Glu Glu Lys Lys Glu Ala Lys Glu Glu Lys Lys Ala Ile Lys
            775                 780                 785

Asn Glu Ala Thr Lys Lys
            790
```

The invention claimed is:

1. A modified *Bacillus subtilis* strain which has had one or more forespore-specific sporulation gene(s) deleted or inactivated compared to the corresponding unmodified *Bacillus subtilis*, and
   which has been transformed with a polynucleotide expressing a target polypeptide down-stream of a transcription initiation regulation region, translational initiation region, or a secretion signal region of an alkaline cellulase gene of *Bacillus*;
   wherein said modified *Bacillus subtilis* expresses an enhanced amount of the target polypeptide compared to the corresponding unmodified *Bacillus subtilis* strain;
   wherein the forespore-specific gene is selected from the group consisting of at least one of sigF, sigG and spoIIE.

2. The recombinant modified *Bacillus subtilis* of claim 1, in which at least one stage II, III, IV or V forespore-specific sporulation gene has been inactivated or deleted compared to the corresponding unmodified *Bacillus subtilis*.

3. The modified *Bacillus subtilis* strain of claim 1, wherein said forespore-specific sporulation gene has been deleted.

4. The modified *Bacillus subtilis* strain of claim 1, wherein said forespore-specific sporulation gene has been inactivated.

5. The modified *Bacillus subtilis* strain of claim 1, which has been transformed with a polynucleotide expressing a target polypeptide which is an enzyme.

6. The modified *Bacillus subtilis* strain of claim 1, which has been transformed with a polynucleotide expressing a target polypeptide which is an enzyme selected from the group consisting of an oxidoreductase, a transferase, a hydrolase, a lyase, an isomerase, and a ligase/synthetase.

7. The modified *Bacillus subtilis* strain of claim 1, which has been transformed with a polynucleotide expressing a target polypeptide which is a hydrolase selected from the group consisting of a cellulase, an α-amylase, and a protease.

8. The modified *Bacillus subtilis* strain of claim 1, which has been transformed with a polynucleotide expressing a target polypeptide which is a *Bacillus subtilis* cellulase.

9. The modified *Bacillus subtilis* strain of claim 1, which has been transformed with a polynucleotide expressing a target polypeptide which is SEQ ID NO: 2 or SEQ ID NO: 4.

10. The modified *Bacillus subtilis* strain of claim 1, wherein said transcription initiation regulation region, translational initiation region, or a secretion signal region is from *Bacillus subtilis*.

11. The modified *Bacillus subtilis* strain of claim 1, wherein said transcription initiation regulation region, translational initiation region, or a secretion signal region is a transcriptional initiation region regulation region containing a promoter and a transcriptional initiation point.

12. The modified *Bacillus subtilis* strain of claim 1, wherein said transcription initiation regulation region, translational initiation region, or a secretion signal region is a translation initiation region containing a ribosome binding site and an initiation codon.

13. The modified *Bacillus subtilis* strain of claim 1, wherein said transcription initiation regulation region, translational initiation region, or a secretion signal region is a secretion signal peptide.

14. The modified *Bacillus subtilis* strain of claim 1, wherein said transcription initiation regulation region, translational initiation region, or a secretion signal region is contained within SEQ ID NO: 1 or 3.

15. The modified *Bacillus subtilis* strain of claim 1, wherein said forespore-specific sporulation gene which has been deleted or inactivated is sigF.

16. The modified *Bacillus subtilis* strain of claim 1, wherein said forespore-specific sporulation gene which has been deleted or inactivated is spoIIE.

17. The modified *Bacillus subtilis* strain of claim 1, wherein said forespore-specific sporulation gene which has been deleted or inactivated is sigG.

* * * * *